United States Patent [19]

Willey

[11] Patent Number: 5,639,606
[45] Date of Patent: Jun. 17, 1997

[54] METHOD FOR QUANTITATIVE MEASUREMENT OF GENE EXPRESSION USING MULTIPLEX COMPETITIVE REVERSE TRANSCRIPTASE-POLYMERASE CHAIN REACTION

[75] Inventor: James C. Willey, Rochester, N.Y.

[73] Assignee: The University of Rochester, Rochester, N.Y.

[21] Appl. No.: 188,434

[22] Filed: Jan. 28, 1994

Related U.S. Application Data

[63] Continuation-in-part of Ser. No. 43,390, Apr. 6, 1993.

[51] Int. Cl.$^6$ .............. C12Q 1/68; C12Q 1/70; C12P 19/34; C07H 21/04
[52] U.S. Cl. .............. 435/6; 435/5; 435/91.1; 435/91.2; 536/24.3; 536/24.32; 536/24.33; 536/23.1
[58] Field of Search .............. 435/6, 69.1, 91.1, 435/91.2, 810; 436/501, 63; 536/22.1, 23.1, 24.1, 24.3–24.33; 935/77, 78, 88

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis et al. | 435/91.2 |
| 4,965,188 | 10/1990 | Mullis et al. | 435/6 |
| 5,213,961 | 5/1993 | Bunn et al. | 435/6 |
| 5,219,727 | 6/1993 | Wang et al. | 436/6 |

OTHER PUBLICATIONS

Araki et al., Rapid and Sensitive Method for Quantitation of Bone Gla Protein mRNA Using Competitive Polymerase Chain Reaction, Journal of Bone and Mineral Research, vol. 8(3) 313–321, Mar., 1993.
Dukas et. al. Quantitation of Charges in the Expression of Multiple Genes by Simultaneous PCR, Anal Biochem 215 66–72, 1993.
Gilliard et al PNAS 87: 2725–2729, Apr. 1991.
Higuchi et al Nucleic Acids Research 16: 7351–7367, 1988.
Pannetier et al Nucleic Acids Research 21: 577–583, 1993.
Apostolakos et al Analytical Biochem 213: 277–284, 1983.
Becker–Andre et al. NAR 25: 9437–9445 1989.
Chelly et al. Nature 333: 858–860 1988.
Gilliland, G., et al., Proc. Natl. Acad. Sci. 87: 2725–2729 (1990).
Horikoshi, T., et al., Cancer Res. 52:108–116 (1992).
Noonan, K.E., et al., Proc. Natl. Acad. Sci. 87:7160–7164 (1990).
Murphy, L.D., et al., Biochemistry 29:10351–10356 (1990).
Carre, P.C., et al., J. Clin. Invest. 88:1802–1810 (1991).
Chelly, J., et al., Eur. J. Biochem 187:691–698 (1990).
Abbs, S., et al., J. Med. Genet. 29:191–196 (1992).
Feldman, A.M. et al., Circulation 83:1866–1872 (1991).
Siebert, P.D., et al., Nature 359:557–558 (1992).
Siebert, P.D., et al., Bio Techniques 14:244–249 (1993).
Clontech Brochure, 1993, Reverse Transcriptase–PCR (RT–PCR).
Celi et al, Nucleic Acids Res., 21, 1047 (1993).
Devereux et al. N A R 12 387 (1984).
Barbu et al., N A R 17 7115 (1989).
Willey et al, Cancer Res. 51:5370–5377 (1990).
Chomczynski and Sacchi (Analytical Biochemistry 162:156–159 (1987).
Chada et al., Genomics 6:268–271 (1990).
Tso et al., Nucleic Acids Res. 13:2485–2502 (1985).
Becker–Andre et al., Nucleic Acids Res. 17:9437–9446 (1989).
Jaiswal, et al., Science 228:80–83 (1985).
Apostolakos et al., Anal. Biochem. 213:277–284 (1993).
Overby et al., Mol. Pharmacology 41:1039–1046 (1992).

Primary Examiner—W. Gary Jones
Assistant Examiner—Dianne Rees
Attorney, Agent, or Firm—Emch, Schaffer, Schaub & Porcello

[57] ABSTRACT

A method for quantitative measurement of gene expression through multiplex competitive reverse transcriptase polymerase chain reaction amplification is established. This method is especially useful for analysis of small specimens of cells and tissues.

6 Claims, 6 Drawing Sheets

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear (ii) MOLECULE TYPE: cDNA (iii) HYPOTHETICAL: NO (iv) ANTI-SENSE: NO (v) FRAGMENT TYPE: internal (vi) ORIGINAL SOURCE:
  (A) ORGANISM: Homo Sapiens
  (H) CELL LINE: HL-60

(x) PUBLICATION INFORMATION:
  (A) AUTHORS: Chada, S.
      Le Beau, M. M.
      Casey, L.
      Newberger, P. E.
  (C) JOURNAL: Genomics
  (D) VOLUME: 6
  (F) PAGES: 268-271
  (G) DATE: September-1990

(xi) SEQUENCE DESCRIPTION: SEQ ID NO:1:

GGGGCCTGGT GGTGCTCGGC T                                             21

(2) INFORMATION FOR SEQ ID NO:2:

(i) SEQUENCE CHARACTERISTICS:
    (A) LENGTH: 21 base pairs
    (B) TYPE: nucleic acid
    (C) STRANDEDNESS: double
    (D) TOPOLOGY: linear (ii) MOLECULE TYPE: cDNA (iii) HYPOTHETICAL: NO (iv) ANTI-SENSE: NO (v) FRAGMENT TYPE: internal (vi) ORIGINAL SOURCE:
    (A) ORGANISM: Homo Sapiens
    (H) CELL LINE: HL-60

(x) PUBLICATION INFORMATION:
    (A) AUTHORS: Chada, S.
        Le Beau, M. M.
        Casey, L.
        Newberger, P. E.
    (C) JOURNAL: Genomics
    (D) VOLUME: 6
    (F) PAGES: 268-271
    (G) DATE: September-1990

(xi) SEQUENCE DESCRIPTION: SEQ ID NO:2:

CAATGGTCTG GAAGCGGCGG C                                             21

(2) INFORMATION FOR SEQ ID NO:3:

(i) SEQUENCE CHARACTERISTICS:
    (A) LENGTH: 30 base pairs
    (B) TYPE: nucleic acid
    (C) STRANDEDNESS: double
    (D) TOPOLOGY: linear (ii) MOLECULE TYPE: cDNA (iii) HYPOTHETICAL: NO (iv) ANTI-SENSE: NO (v) FRAGMENT TYPE: internal (vi) ORIGINAL SOURCE:
    (A) ORGANISM: Homo Sapiens ( D ) DEVELOPMENTAL STAGE: Adult
          ( H ) CELL LINE: HL-60

( x ) PUBLICATION INFORMATION:
          ( A ) AUTHORS: Chada, S.
                        Le Beau, M. M.
                        Casey, L.
                        Newberger, P. E.
          ( C ) JOURNAL: Genomics
          ( D ) VOLUME: 6
          ( F ) PAGES: 268-271
          ( G ) DATE: 1990

( x i ) SEQUENCE DESCRIPTION: SEQ ID NO:3:

ATTCTGATTT CCCTCAAGTA CGTCCGGCCT                                                         30

( 2 ) INFORMATION FOR SEQ ID NO:4:

( i ) SEQUENCE CHARACTERISTICS:
          ( A ) LENGTH: 30 base pairs
          ( B ) TYPE: nucleic acid
          ( C ) STRANDEDNESS: double
          ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: internal ( v i ) ORIGINAL SOURCE:
          ( A ) ORGANISM: Homo Sapiens
          ( D ) DEVELOPMENTAL STAGE: Adult
          ( H ) CELL LINE: HL-60

( x ) PUBLICATION INFORMATION:
          ( A ) AUTHORS: Chada, S.
                        Le Beau, M. M.
                        Casey, L.
                        Newberger, P. E.
          ( C ) JOURNAL: Genomics
          ( D ) VOLUME: 6
          ( F ) PAGES: 268-271
          ( G ) DATE: 1990

( x i ) SEQUENCE DESCRIPTION: SEQ ID NO:4:

TAAGACTAAA GGGAGTTCAT GCAGGCCGGA                                                         30

( 2 ) INFORMATION FOR SEQ ID NO:5:

( i ) SEQUENCE CHARACTERISTICS:
          ( A ) LENGTH: 25 base pairs
          ( B ) TYPE: nucleic acid
          ( C ) STRANDEDNESS: double
          ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: internal ( v i ) ORIGINAL SOURCE:
          ( A ) ORGANISM: Homo Sapiens
          ( D ) DEVELOPMENTAL STAGE: Adult
          ( F ) TISSUE TYPE: Liver
          ( G ) CELL TYPE: Hepatocellular ( x ) PUBLICATION INFORMATION:
          ( A ) AUTHORS: Tso, J. Y.
                        Sun, X.
                        Kao, T.

Reese, K. S.
Wu, R.
( C ) JOURNAL: Nucleic Acids Research
( D ) VOLUME: 13
( F ) PAGES: 2485-2502
( G ) DATE: 1985

( x i ) SEQUENCE DESCRIPTION: SEQ ID NO:5:

GGTCGGGAGT CAACGGATTT GGTCG                                     25

( 2 ) INFORMATION FOR SEQ ID NO:6:

( i ) SEQUENCE CHARACTERISTICS:
      ( A ) LENGTH: 22 base pairs
      ( B ) TYPE: nucleic acid
      ( C ) STRANDEDNESS: double
      ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: internal ( v i ) ORIGINAL SOURCE:
      ( A ) ORGANISM: Homo Sapiens
      ( D ) DEVELOPMENTAL STAGE: Adult
      ( F ) TISSUE TYPE: Liver
      ( G ) CELL TYPE: Hepatocellular ( x ) PUBLICATION INFORMATION:
      ( A ) AUTHORS: Tso, J. Y.
            Sun, X.
            Kao, T.
            Reece, K. S.
            Wu, R.
      ( C ) JOURNAL: Nucleic Acids Research
      ( D ) VOLUME: 13
      ( F ) PAGES: 2485-2502
      ( G ) DATE: 1985

( x i ) SEQUENCE DESCRIPTION: SEQ ID NO:6:

CCTCCGACGC CTGCTTCACC AC                                        22

( 2 ) INFORMATION FOR SEQ ID NO:7:

( i ) SEQUENCE CHARACTERISTICS:
      ( A ) LENGTH: 24 base pairs
      ( B ) TYPE: nucleic acid
      ( C ) STRANDEDNESS: double
      ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: internal ( v i ) ORIGINAL SOURCE:
      ( A ) ORGANISM: Homo Sapiens
      ( D ) DEVELOPMENTAL STAGE: Adult
      ( F ) TISSUE TYPE: Liver
      ( G ) CELL TYPE: Hepatocellular ( x ) PUBLICATION INFORMATION:
      ( A ) AUTHORS: Tso, J. Y.
            Sun, X.
            Kao, T.
            Reece, K. S.
            Wu, R.
      ( C ) JOURNAL: Nucleic Acids Research
      ( D ) VOLUME: 13

(F) PAGES: 2485-2502
(G) DATE: 1985

(xi) SEQUENCE DESCRIPTION: SEQ ID NO:7:

TGATCAATGG AATTCCCATC ACCA 24

(2) INFORMATION FOR SEQ ID NO:8:

(i) SEQUENCE CHARACTERISTICS:
(A) LENGTH: 24 base pairs
(B) TYPE: nucleic acid
(C) STRANDEDNESS: double
(D) TOPOLOGY: linear (ii) MOLECULE TYPE: cDNA (iii) HYPOTHETICAL: NO (iv) ANTI-SENSE: NO (v) FRAGMENT TYPE: internal (vi) ORIGINAL SOURCE:
(A) ORGANISM: Homo Sapiens
(D) DEVELOPMENTAL STAGE: Adult
(F) TISSUE TYPE: Liver
(G) CELL TYPE: Hepatocellular (x) PUBLICATION INFORMATION:
(A) AUTHORS: Tso, J. Y.
Sun, X.
Kao, T.
Reece, K. S.
Wu, R.
(C) JOURNAL: Nucleic Acids Research
(D) VOLUME: 13
(F) PAGES: 2485-2502
(G) DATE: 1985

(xi) SEQUENCE DESCRIPTION: SEQ ID NO:8:

ACTAGTTACC TTAAGGGTAG TGGT 24

(2) INFORMATION FOR SEQ ID NO:9:

(i) SEQUENCE CHARACTERISTICS:
(A) LENGTH: 20 base pairs
(B) TYPE: nucleic acid
(C) STRANDEDNESS: double
(D) TOPOLOGY: linear (ii) MOLECULE TYPE: cDNA (iii) HYPOTHETICAL: NO (iv) ANTI-SENSE: NO (v) FRAGMENT TYPE: internal (vi) ORIGINAL SOURCE:
(A) ORGANISM: Homo Sapiens
(D) DEVELOPMENTAL STAGE: Adult
(F) TISSUE TYPE: Liver
(G) CELL TYPE: Hepatocellular (x) PUBLICATION INFORMATION:
(A) AUTHORS: Tso, J. Y.
Sun, X.
Kao, T.
Reece, K. S.
Wu, R.
(C) JOURNAL: Nucleic Acids Research
(D) VOLUME: 13
(F) PAGES: 2485-2502
(G) DATE: 1985

(xi) SEQUENCE DESCRIPTION: SEQ ID NO:9:

CATGGCACCG TCAAGGCAAC                                                                                           20

( 2 ) INFORMATION FOR SEQ ID NO:10:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: Homo Sapiens
        ( D ) DEVELOPMENTAL STAGE: Adult
        ( F ) TISSUE TYPE: Liver
        ( G ) CELL TYPE: Hepatocellular ( x ) PUBLICATION INFORMATION:
        ( A ) AUTHORS: Tso, J. Y.
                Sun, X.
                Kao, T.
                Reece, K. S.
                Wu, R.
        ( C ) JOURNAL: Nucleic Acids Research
        ( D ) VOLUME: 13
        ( F ) PAGES: 2485-2502
        ( G ) DATE: 1985

( x i ) SEQUENCE DESCRIPTION: SEQ ID NO:10:

CCTCCGACGC CTGCTTCACC AC                                                                                        22

( 2 ) INFORMATION FOR SEQ ID NO:11:

( i ) SEQUENCE CHARACTERISTICS:
        ( A ) LENGTH: 26 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: Homo Sapiens
        ( D ) DEVELOPMENTAL STAGE: Adult
        ( F ) TISSUE TYPE: Liver ( x ) PUBLICATION INFORMATION:
        ( A ) AUTHORS: Tso, J. Y.
                Sun, X.
                Kao, T.
                Reece, K. S.
                Wu, R.
        ( C ) JOURNAL: Nucleic Acids Research
        ( D ) VOLUME: 13
        ( F ) PAGES: 2485-2502
        ( G ) DATE: 1985

( x i ) SEQUENCE DESCRIPTION: SEQ ID NO:11:

CAGGGGGGAT CCAAAAGGGT CATCAT                                                                                    26

( 2 ) INFORMATION FOR SEQ ID NO:12:

( i ) SEQUENCE CHARACTERISTICS:
    ( A ) LENGTH: 26 base pairs
    ( B ) TYPE: nucleic acid
    ( C ) STRANDEDNESS: double
    ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: internal ( v i ) ORIGINAL SOURCE:
    ( A ) ORGANISM: Homo Sapiens
    ( D ) DEVELOPMENTAL STAGE: Adult
    ( F ) TISSUE TYPE: Liver ( x ) PUBLICATION INFORMATION:
    ( A ) AUTHORS: Tso, J. Y.
        Sun, X.
        Kao, T.
        Reese, K. S.
        Wu, R.
    ( C ) JOURNAL: Nucleic Acids Research
    ( D ) VOLUME: 13
    ( F ) PAGES: 2485-2502
    ( G ) DATE: 1985

( x i ) SEQUENCE DESCRIPTION: SEQ ID NO:12:

GTCCCCCCTA GGTTTTCCCA GTAGTA                                26

( 2 ) INFORMATION FOR SEQ ID NO:13:

( i ) SEQUENCE CHARACTERISTICS:
        ( A ) LENGTH: 24 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Homo sapiens
        ( F ) TISSUE TYPE: Liver ( x ) PUBLICATION INFORMATION:
        ( A ) AUTHORS: Tokunaga, K.
            Nakamura, Y.
            Sakata, K.
            Fujimori, K.
            Ohkubo, M.
            Sawada, K.
            Sakiyama, S.
        ( B ) TITLE: Enhanced expression of a
            glyceraldehyde-3-phosphate dehydrogenase gene in
            human lung cancers
        ( C ) JOURNAL: Cancer Res.
        ( D ) VOLUME: 47
        ( F ) PAGES: 5616-5619
        ( G ) DATE: SUMMER-1990
        ( K ) RELEVANT RESIDUES IN SEQ ID NO:13: FROM 1 TO 24

( x i ) SEQUENCE DESCRIPTION: SEQ ID NO:13:

GGTCGGAGTC AACGGATTTG GTCG                                  24

( 2 ) INFORMATION FOR SEQ ID NO:14:

( i ) SEQUENCE CHARACTERISTICS:
        ( A ) LENGTH: 40 base pairs ( B ) TYPE: nucleic acid
            ( C ) STRANDEDNESS: single
            ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
            ( A ) ORGANISM: Homo Sapiens
            ( D ) DEVELOPMENTAL STAGE: Adult
            ( F ) TISSUE TYPE: Lung
            ( G ) CELL TYPE: Bronchial epithelial
            ( H ) CELL LINE: Lung cancer ( x ) PUBLICATION INFORMATION:
            ( A ) AUTHORS: Tokunaga, K.
                    Nakamura, Y.
                    Sakata, K.
                    Fujimora, K.
                    Ohkubo, M.
                    Sawada, K.
                    Sakiyama, S.
            ( B ) TITLE: Enhanced expression of a
                    glyceraldehyde-3-phosphate dehydrogenase gene in
                    human lung cancers
            ( C ) JOURNAL: Cancer Res.
            ( D ) VOLUME: 47
            ( F ) PAGES: 5616-5619
            ( G ) DATE: Summer-1990
            ( K ) RELEVANT RESIDUES IN SEQ ID NO:14: FROM 1 TO 40

( x i ) SEQUENCE DESCRIPTION: SEQ ID NO:14:

CCTCCGACGC CTGCTTCACC CCATCACGCC ACAGTTTCCC                    40

( 2 ) INFORMATION FOR SEQ ID NO:15:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
            ( A ) ORGANISM: Homo Sapiens
            ( D ) DEVELOPMENTAL STAGE: Adult
            ( F ) TISSUE TYPE: Lung
            ( G ) CELL TYPE: Bronchial epithelial
            ( H ) CELL LINE: Lung cancer ( x ) PUBLICATION INFORMATION:
            ( A ) AUTHORS: Tokunaga, K.
                    Nakamura, Y.
                    Sakata, K.
                    Fujimora, K.
                    Ohkubo, M.
                    Sawada, K.
                    Sakiyama, S.
            ( B ) TITLE: Enhanced expression of a
                    glyceraldehyde-3-phosphate dehydrogenase gene in
                    human lung cancers
            ( C ) JOURNAL: Cancer Res.
            ( D ) VOLUME: 47
            ( F ) PAGES: 5616-5619
            ( G ) DATE: summer-1990
            ( K ) RELEVANT RESIDUES IN SEQ ID NO:15: FROM 1 TO 20

( x i ) SEQUENCE DESCRIPTION: SEQ ID NO:15:

CCTCCGACGC CTGCTTCACC                                          20

( 2 ) INFORMATION FOR SEQ ID NO:16:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: Homo Sapiens
        ( D ) DEVELOPMENTAL STAGE: Adult
        ( F ) TISSUE TYPE: Breast
        ( G ) CELL TYPE: Mammary epithelial
        ( H ) CELL LINE: MCF-7

( x ) PUBLICATION INFORMATION:
        ( A ) AUTHORS: Jaiswal, A. K.
              Gonzalez, F. J.
              Nebert, D. W.
        ( B ) TITLE: Human dioxin-inducible cytochrome P-1-450
        ( T C D D - i n d u c i b l e ) mRNA, complete cds.
        ( C ) JOURNAL: Science
        ( D ) VOLUME: 228
        ( F ) PAGES: 80-83
        ( G ) DATE: 15-JUN-1989
        ( K ) RELEVANT RESIDUES IN SEQ ID NO:16: FROM 1 TO 21

( x i ) SEQUENCE DESCRIPTION: SEQ ID NO:16:

CATCCCCCAC AGCACAACAA G          21

( 2 ) INFORMATION FOR SEQ ID NO:17:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: Homo Sapiens
        ( D ) DEVELOPMENTAL STAGE: Adult
        ( F ) TISSUE TYPE: Breast
        ( G ) CELL TYPE: Mammary epithelial
        ( H ) CELL LINE: MCF-7

( x ) PUBLICATION INFORMATION:
        ( A ) AUTHORS: Jaiswal, A. K.
              Gonzalez, F. J.
              Nebert, D. W.
        ( B ) TITLE: Human dioxin-inducible cytochrome P1-450:
            Complementary DNA and amino acid sequence
        ( C ) JOURNAL: Science
        ( D ) VOLUME: 228
        ( F ) PAGES: 80-83
        ( G ) DATE: 15-JUN-1989
        ( K ) RELEVANT RESIDUES IN SEQ ID NO:17: FROM 1 TO 40

( x i ) SEQUENCE DESCRIPTION: SEQ ID NO:17:

ACAGCAGGCA TGCTTCATGG GTCTCACCGA TACACTTCCG          40

( 2 ) INFORMATION FOR SEQ ID NO:18:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
    ( A ) ORGANISM: Homo Sapiens
    ( D ) DEVELOPMENTAL STAGE: Adult
    ( F ) TISSUE TYPE: Breast
    ( G ) CELL TYPE: Mammary epithelial
    ( H ) CELL LINE: MCF-7

( x ) PUBLICATION INFORMATION:
    ( A ) AUTHORS: Jaiswal, A. K.
            Gonzalez, F. J.
            Nebert, D. W.
    ( B ) TITLE: Human dioxin-inducible cytochrome P1-450:
            Complementary DNA and amino acid sequence
    ( C ) JOURNAL: Cancer Res.
    ( D ) VOLUME: 228
    ( F ) PAGES: 80-83
    ( G ) DATE: 15-JUN-1989
    ( K ) RELEVANT RESIDUES IN SEQ ID NO:18: FROM 1 TO 20

( x i ) SEQUENCE DESCRIPTION: SEQ ID NO:18:

ACAGCAGGCA TGCTTCATGG                                             20

METHOD FOR QUANTITATIVE MEASUREMENT OF GENE EXPRESSION USING MULTIPLEX COMPETITIVE REVERSE TRANSCRIPTASE-POLYMERASE CHAIN REACTION

The present invention was made under research grant number ES02679 and ES01247 from the National Institute of Health, Grant No. RR00044 from the Division of Research Resources, Health Institute Contract 91-2 and International Lead Zinc Organization Contract CH611 who may have certain rights thereto. The present invention relates generally to a method for the quantitative measurement of cellular levels of RNA following reverse transcription and polymerase chain reaction (PCR) amplification.

This is a continuation in part of Ser. No. 08/043,390 filed Apr. 6, 1993.

TECHNICAL BACKGROUND

The PCR techniques are generally described in U.S. Pat. Nos. 4,683,195; 4,683,202; and 4,965,188. The PCR technique generally involves a process for amplifying any desired specific nucleic acid sequence contained within a nucleic acid sequence which is within a nucleic acid molecule. The PCR process includes treating separate complementary strains of the nucleic acid with an excess of two oligonucleotide primers. The primers are extended to form complementary primer extension products which act as templates for synthesizing the desired nucleic acid sequence. The PCR process is carried out in a simultaneous step-wise fashion and can be repeated as often as desired in order to achieve increased levels of amplification of the desired nucleic acid sequence. According to the PCR process, the sequence of DNA between the primers on the respective DNA strains are amplified selectively over the remaining portions of the DNA and selected sample. The PCR process provides for the specific amplification of a desired region of DNA.

The yield of product from PCR increases exponentially for an indefinite number of cycles. At some point and for uncertain reasons, the reaction becomes limited and PCR product increases at an unknown rate. Consequently, the yield of amplified product has been reported to vary by as much as 6-fold between identical samples run simultaneously. (Gilliland, G., et al., *Proc. Natl. Acad. Sci.* 87:2725-2729, 1990). (These publications and other reference materials have been included to provide additional details on the background of the invention and, in particular instances, the practice of the invention, and all are expressly incorporated herein by reference.) Therefore, after a certain number of PCR cycles, the initial concentrations of target DNA cannot be accurately determined by extrapolation. In an attempt to make PCR quantitative, various investigators have analyzed samples amplified for a number of cycles known to provide exponential amplification (Horikoshi, T., et al., *Cancer Res.* 52:108-116 (1992); Noonan, K. E., et al., *Proc. Natl. Acad. Sci.* 87:7160-7164 (1990); Murphy, L. D., et al., *Biochemistry* 29:10351-10356 (1990); Carre, P. C., et al., *J. Clin. Invest.* 88:1802-1810 (1991); Chelly, J., et al., *Eur. J. Biochem* 187:691-698 (1990); Abbs, S., et al., *J. Med. Genet.* 29:191-196 (1992); Feldman, A. M. et al., *Circulation* 83:1866-1872 (1991). In general, these analyses are done early in the PCR process when the PCR product is measurable by use of radiolabeled probes and autoradiography but not by spectrophotometry or densitometry of ethidium bromide stained gels. The use of radioactivity is inconvenient, expensive, and presents safety concerns. Also, the exponential phase must be defined for each set of experimental conditions, requiring additional cost in time and materials.

Another development is competitive PCR, wherein PCR is conducted in the presence of single base mutated competitive templates (Gilliland, supra; Becker-Andre, et al., *Nucleic Acids Res.* 17:9437-9446 (1989)). A known amount of competitive template is co-amplified with an unknown amount of target sequence. The competitor is the same sequence (except for single base mutation or deletion of a portion of the sequence) as the target, uses the same primers for amplification as the target cDNA, and amplifies with the same efficiency as the target cDNA. The starting ratio of target/standard is preserved throughout the entire amplification process, even after the exponential phase is complete.

Competitive PCR is discussed in general in Siebert, P. D., et al., *Nature* 359:557-558 (1992); Siebert, P. D., et al., *BioTechniques* 14:244-249 (1993), and Clontech Brochure, 1993, Reverse Transcriptase-PCR (RT-PCR). However, competitive PCR alone does not adequately control for variation in starting amounts of template. Degradation of samples and pipetting errors can lead to variation. When using Northern analysis to measure gene expression, it is possible to overcome these problem by probing the same blot for both a target gene and a "housekeeping" gene which is not expected to vary among tissue samples or in response to stimuli. The "housekeeping" gene acts as a denominator in determining the relative expression of a target gene. In attempts to apply this concept, other investigators have PCR-amplified in separate tubes. However, when the two genes are amplified in separate tubes, intertube variation in amplification conditions and pipetting errors are unavoidable. While non-competitive multiplex PCR, where the target and "housekeeping" gene are amplified in the same tube, has also been described in Noonan, supra, this method is inconvenient because it requires the generation of standard curves to determine the exponential range of amplification nuclides.

Therefore, there is a need for quantitative measurement of gene expression technique which has none of the above-described drawbacks and which can be performed by a technician with standard training. The present invention addresses these needs in the art by providing a technique which can be utilized with any PCR process and which can be performed in a simple and straightforward manner. The present invention involves a dramatic improvement over previously described approaches to DNA analysis and the PCR techniques.

SUMMARY OF THE INVENTION

The method of the present invention is an improvement upon the PCR amplification process that allows simultaneous amplification of a "target gene", a "housekeeping" gene and competitive templates for each of these genes. According to the present invention, the terms "target DNA sequence" and "target gene" generally refer to a gene of interest for which there is a desire to selectively amplify that gene or DNA sequence. The term "housekeeping" gene refers to genes that are suitable as internal standards for amount of RNA per PCR reaction. In a general and overall sense, a key to the present invention is the simultaneous use of primers for a target gene, primers for a housekeeping gene, and two internal standard competitive templates comprising mutants of the target gene and housekeeping gene. These mutations can be point mutations, insertions, deletions or the like.

In a broad sense, the present invention is directed to a method for quantifying the amount of a target DNA sequence within an identified region of a selected cDNA molecule that is present within a heterogenous mixture of cDNA molecules. It is to be understood that more than one targeted gene and/or housekeeping gene can be utilized and further that quantitation of such additional target and/or housekeeping genes will necessitate the further inclusion of an internal standard competitive template comprising a mutation of that additional target and/or housekeeping gene. It is to be understood that the mutated competitive templates comprise at least one nucleotide that is mutated relative to the corresponding nucleotide of the target sequence. It is to be noted that mutation of only a single nucleotide that is complementary to the corresponding nucleotide of the housekeeping gene sequence is required for the successful practice of the present invention. However, it is understood that longer deletions, insertions or alterations are useful in the present invention. The target gene primers (which serve as primers for both the native and competitive templates of the target gene), housekeeping gene primers (which serve as primers for both the native and competitive template of the housekeeping gene), competitive template of the target gene, and competitive template of the housekeeping gene are subjected to a PCR process along with native cDNA which contains the DNA for both the target gene and the housekeeping gene. The PCR process provides cDNA products of 1) native cDNA of the target gene and the housekeeping gene and 2) mutated competitive template cDNA of the target gene and the housekeeping gene. The cDNA products are isolated using methods suitable for isolating cDNA products. The relative presence of the native cDNA products and the mutated cDNA products are detected by measuring the amounts of native cDNA coding for the target gene and mutated cDNA coding for the competitive template of the target gene as compared to the amounts of native cDNA coding for the housekeeping gene and mutated cDNA coding for competitive template of the housekeeping gene.

In a further aspect, the present invention concerns novel nucleic acid primer molecules for use in PCR processes for determining the amount of a target DNA sequence.

According to the present invention herein "a sample" generally indicates a sample of tissue or fluid isolated from a plant, individual or in vitro cell culture constituents.

The terms primers, nucleic acids and oligonucleotides are understood to refer to polyribonucleotides and polydeoxyribonucleotides and there is no intended distinction in the length of sequences referred to by these terms. Rather, these terms refer to the primary structure of the molecule. These terms include double and single stranded RNA and double and single stranded DNA. It is to be understood that the oligonucleotides can be derived from any existing or natural sequence and generated in any manner. It is further understood that the oligonucleotides can be generated from chemical synthesis, reverse transcription, DNA replication and a combination of these generating methods. The term "primer" generally refers to an oligonucleotide capable of acting as a point of initiation of synthesis along a complementary strand when conditions are suitable for synthesis of a primer extension product. The snythesizing conditions include the presence of four different deoxyribonucleotide triphosphates and at least one polymerization-inducing agent such as reverse transcriptase or DNA polymerase. These are present in a suitable buffer which may include constituents which are co-factors or which affect conditions such as pH and the like at various suitable temperatures. It is understood that while a primer is preferably a single strand sequence, such that amplification efficiency is optimized, other double stranded sequences can be practiced with the present invention.

The terms "target gene", "sequence" or "target nucleic acid sequence" are meant to refer to a region of a oligonucleotide which is either to be amplified and/or detected. It is to be understood that the target sequence resides between the primer sequences used in the amplification process.

According to one embodiment of the present invention, quantitative gene expression is measured by multiplex competitive PCR amplification of a) cDNA from at least one target gene of interest and at least one "housekeeping" gene and b) internal mutated standard competitive templates comprising base mutants of the target gene of interest and the "housekeeping" gene cDNA that cause either a loss or gain of a restriction endonuclease recognition site. According to another embodiment, the method comprises the PCR amplification of a) cDNA from at least one target gene of interest and at least one "housekeeping" gene and b) competitive templates comprising sequences of the target gene of interest and the "housekeeping" gene that have been artificially shortened. These shortened sequences retain sequences homologous to both the target gene and the housekeeping gene primers used in PCR amplification. RNA extracted from sample cells or tissues are reverse transcribed. Serial dilutions of cDNA are PCR amplified in the presence of oligonucleotides homologous to the target gene and the "housekeeping" gene, and quantified amounts of internal mutated standard competitive templates. The amplified DNA is restriction digested and electrophoresed on an agarose gel stained with ethidium bromide, separating native from mutated products. Densitometry is performed to quantify the bands. This technique to measure the relative expression of a target gene to a "housekeeping" gene is precise and reproducible for studies done with the same master mixture and dilution of internal standards. Ratios of relative gene expression vary less than 25% from the mean. This technique is useful to measure changes in gene expression. This method is particularly useful when the amount of study sample is limited or the level of gene expression is low.

It is, therefore, the object of the present invention to provide an improved method for quantitative measurement of gene expression.

It is a further object of the present invention to provide a method for quantitative PCR-based measurement of gene expression that is suitable as a commercial process.

These and other objects, features and many of the attendant advantages of the invention will be better understood upon a reading of the following detailed description when considered in connection with the accompanying drawings wherein.

DETAILED DESCRIPTION OF THE INVENTION

Figure 1:
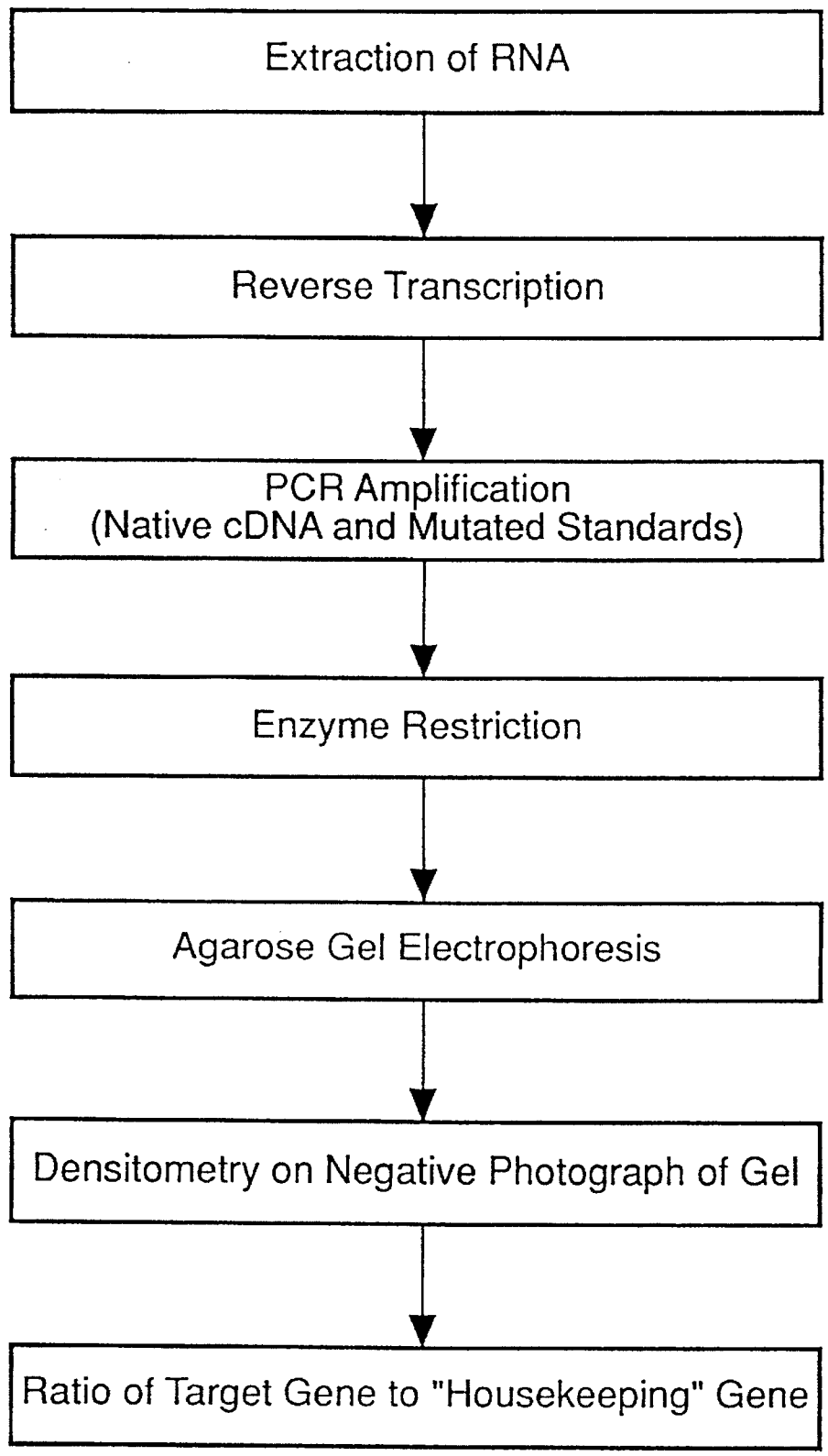
FIG. 1 is a schematic diagram of the work scheme for PCR quantification of relative target gene expression.

For many years, gene expression has been measured through quantification of RNA by Northern or dot blot analysis. These techniques require the amount of RNA obtainable from at least $10^5$ cells for each measurement. Often, a biopsy will provide only the number of cells necessary for a histological diagnosis and this is often far less than $10^5$ cells. Recently developed PCR techniques allow measurement of RNA levels in as few as 100 cells. However, techniques described thus far allow only qualitative, not quantitative measurement.

The present invention relates to a method using multiplex competitive reverse-transcriptase polymerase chain reaction amplification to simplify and improve quantitative measurement of gene expression. DNA extracted from samples is reverse transcribed and then subjected to PCR amplification in the presence of primers for both a "housekeeping" gene and a target gene of interest.

The expression of genes is measured by comparing the amount of at least one target gene to that of a "housekeeping" gene. There are various suitable housekeeping genes which are useful with the present invention, including, for example, such housekeeping genes that have been used as internal standards in Northern analyses of gene expression, including GAPDH, β-actin, 28S RNA and 18S RNA and ribonuclear proteins (Devereux et al., Nucleic Acids Res. 12:387 (1984); Barbu et al., Nucleic Acids Res. 17:7115 (1989). According to one embodiment of the present invention, synthesized oligonucleotides homologous to any sequences containing a known restriction endonuclease recognition site or any sequence containing a one or two-basepair mismatch for a known restriction endonuclease site that is present in the housekeeping gene can be utilized. The application of these restriction endonuclease recognition sites is to either mutate the naturally occurring sites to non-recognition sites or to mutate the mismatch sites to match sites, in either case creating mutant sequences suitable for internal mutated standard competitive templates. The particular sites in the housekeeping gene used for analysis of any particular other gene depends on the match and mismatch sites that are present in the other gene. One determinant is the size of the DNA fragments that are generated from the housekeeping gene and the target gene. It is desired that these fragments separate well on gel electrophoresis.

Further, all oligonucleotides that contain sequences homologous to sequences in the genes for the housekeeping genes can be used in the present invention. Such homologous sequences may be used to generate artificially shortened competitive templates to the housekeeping genes generated according to the method described by Cell et al., Nucleic Acids Res. 21:1047 (1993).

To identify and match one or two base mismatch sequences for all known recognition sites, it is possible to use the Map program within the Genetics Computer Group software package (Devereux et al., supra, 1984). The cDNA sequences are obtained for each gene, then each gene is evaluated for the presence of the match of one or two base pair mismatch sequences for every known restriction endonuclease. According to the present invention, it is possible to use every gene containing any of these recognition sequences or one or two base pair mismatches of these sequences.

Figure 3:
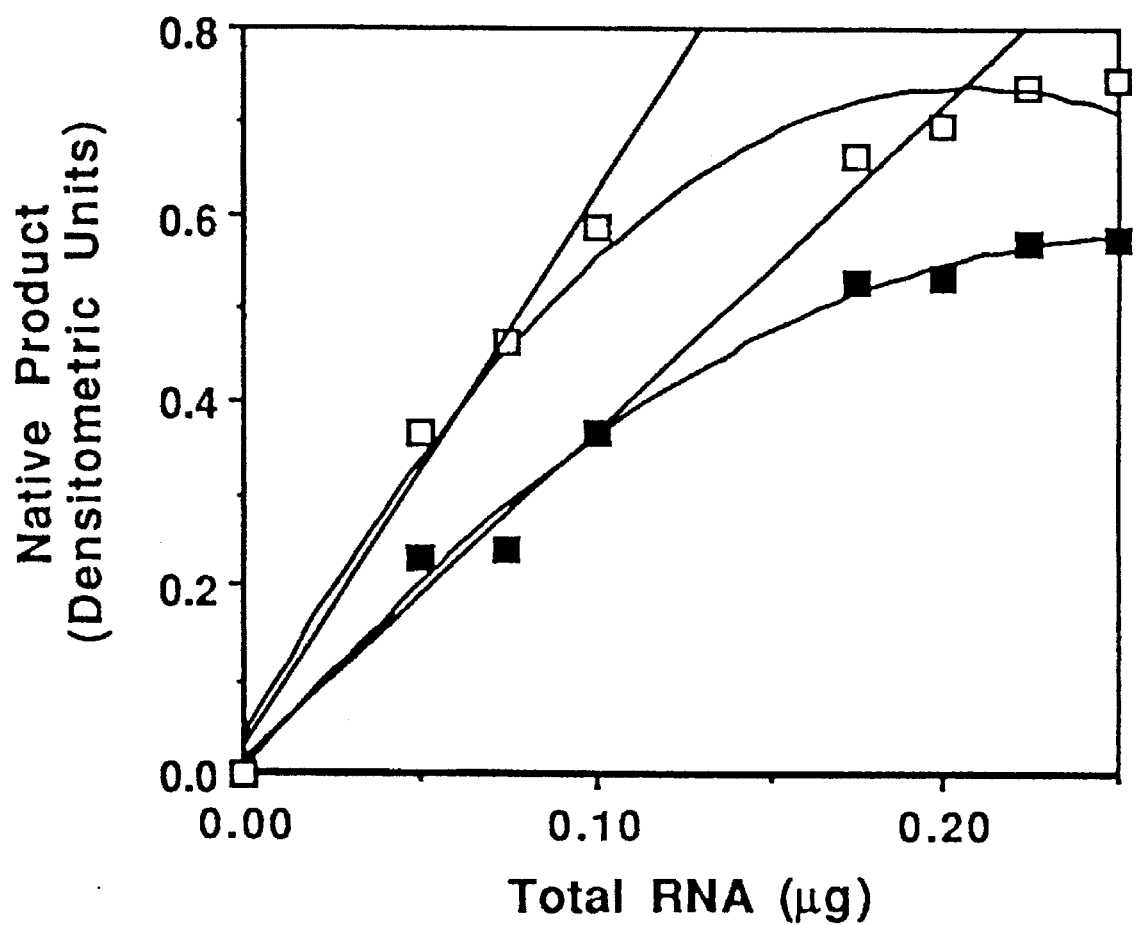
FIG. 3 is a graph showing the native product (☐GSH-Px glutathione peroxidase and ■GAPDH) glyceraldehydesphosphate dehydrogenase vs. total RNA. With small amounts of starting RNA (first three squares for both GSH-Px) and GAPDH), the reactions are exponential throughout, however, with increasing amounts of RNA, the reaction becomes non-exponential at some point during amplification, resulting in less product formation than expected in a non-limited reaction. The straight lines represent the theoretical amounts of PCR product (either GSH-Px or GAPDH) which would have formed if amplification remained exponential throughout the amplification process.
Figure 4:
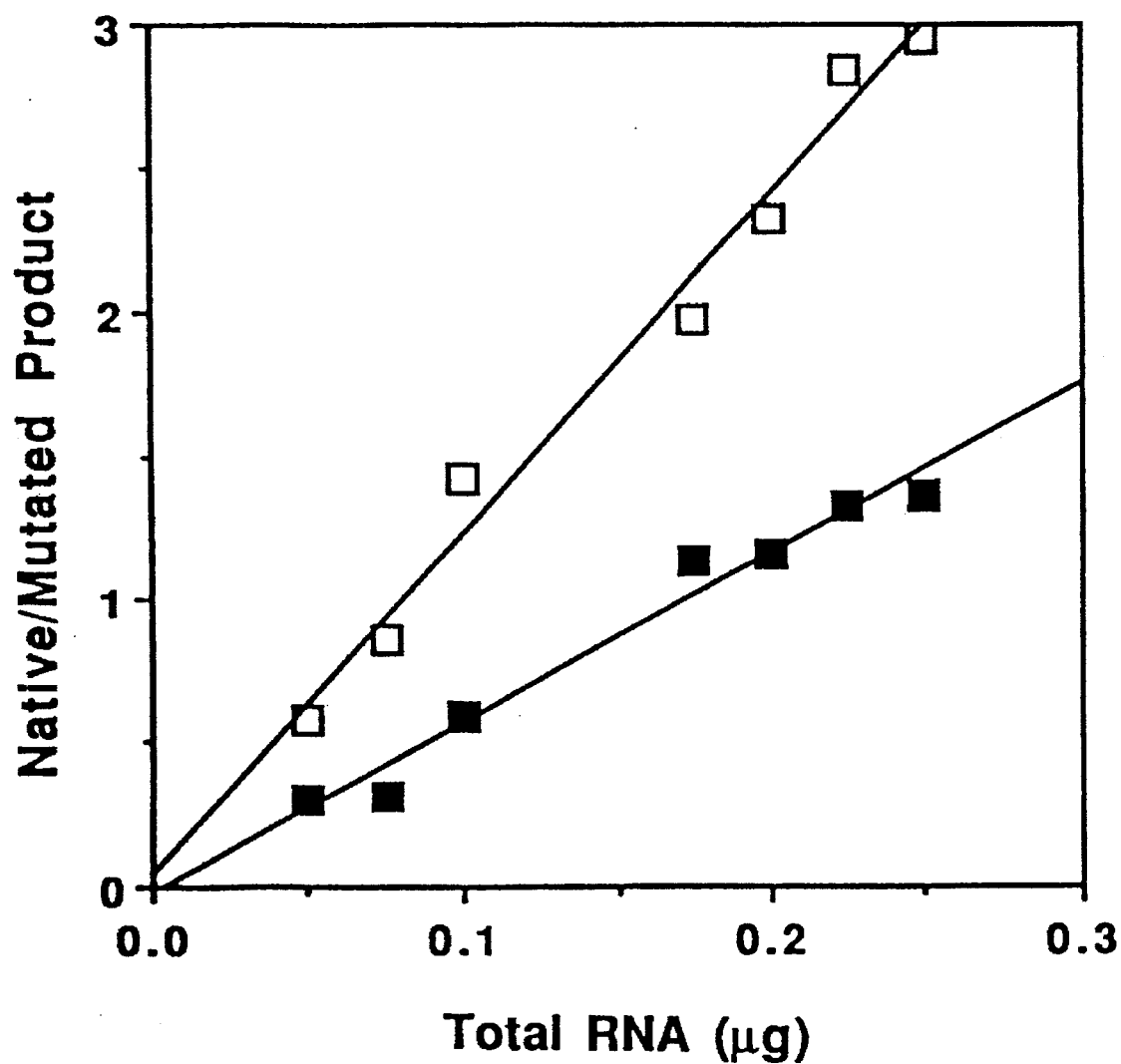
FIG. 4 is a graph showing Native/Mutated amplification products (☐GSH-Px and ■GAPDH) vs. Total RNA. The relationship remains linear for both GSH-Px ($r^2=0.982$) and GAPDH ($r^2=0.973$) throughout the range of total RNA studied. This is consistent with the findings of Gilliland et al., *Proc. Natl. Acad. Sci.*, 87:2725–2729, 1990. This relationship attests to the quantitative nature of multiplex competitive PCR.

The present invention of multiplex competitive PCR (for any given master mixture and dilution of mutated standards) yields reproducible ratios of target gene/housekeeping gene. Because the relationship between the amount of native product vs. total starting RNA does not remain linear with increasing amounts of RNA (FIG. 3), it is clear that the amplification is not exponential throughout. However, consistent target/housekeeping gene ratios are obtained with the use of a competitive template for each. The quantitative results are illustrated by the linear relationship between the native/mutated template ratio vs. total starting RNA for each of the genes (FIG. 4). This illustrates the utility of competitive template internal controls; it is not necessary to remain in the exponential phase of amplification to quantify relative amounts of gene expression. The reproducibility of the ratio between samples in the same study allows for the use of fewer dilution tubes. Only one tube, in which all bands are quantifiable, is necessary for measurement of gene expression. This simplifies the procedure and permits the evaluation of many different samples at one time.

According to one embodiment of the present invention there may be a choice of restriction endonuclease recognition sites used to separate the mutated from native products. In addition, the ultimate length of the PCR product present after restriction endonuclease digestion is a factor to consider. In certain embodiments, agarose gels are more preferable to use than polyacrylamide gels, but require greater DNA fragment size differences for adequate separation (approximately 50–100 base pair differences). The method of the present invention can be further simplified by using the same recognition site for both the target and housekeeping gene. EcoRI sites are often appropriate. In a specific embodiment of the present invention, GAPDH competitive templates were prepared that separate from native GAPDH on the basis of EcoRI or BamHI digestion. However, it is to be understood that separation on the basis of EcoRI or other restriction endonuclease digestion that is compatible with a greater number of genes may also occur.

A large variation (up to 200-fold) in the target housekeeping (GSH-Px/GAPDH) gene expression ratio has been observed in studies performed on BEP2D cDNA using different master mixtures and dilutions of mutated standards.

Since samples that underwent reverse transcription separately gave similar results, the amount of variability introduced at this step is small. Any differences in reaction conditions will equally affect amplification of the competitive template as well as the native template and thus the ratio between the two will remain constant. Therefore, the variability likely results from differences in the amount of internal mutated standard competitive template in the reaction. The concentration of competitive template is so small (femtomolar range) that any change in the number of molecules present in the reaction would introduce a large source of error.

The method of the present invention is precise in any given study as illustrated by the reproducibility between samples using the same master mixture with mutated internal standard competitive templates. Therefore, according to a preferred embodiment, it is desirable that comparative samples be run simultaneously using the same master mixture with the same dilution of internal mutated standard competitive templates.

In a preferred embodiment, the reaction mixture includes the following: a) competitive template for a housekeeping gene, b) competitive template for a target gene of interest, c) oligonucleotide primers for PCR amplification of the housekeeping gene, d) oligonucleotide primers for PCR amplification of the target gene of interest, e) reaction buffer, and f) cDNA from the test sample.

It is also preferred that the PCR conditions be standardized for each experiment by using, for example, a master mixture containing 1× PCR buffer (for example, 50 mM KCl, 10 mM Tris-HCl, 1.5 mM $MgCl_2$), primers coding for the target gene and the housekeeping gene (25 pmoles of each), 0.2 mM dNTP's (A,T,C,G), and constant amounts of each competitive template per 100 μL reaction mixture. TaqDNA polymerase (2.5 units) is added to each 100 μL reaction prior to amplification. PCR amplification is preferably carried out for 35–38 cycles at 94° C. for one min., 60° C. for one min., and 72° C. for one min., or as is optimal for the particular region amplified. After amplification, PCR products are preferably heated for 10 min. and then cooled slowly in order to maximize heterodimer formation.

For reaction using competitive templates mutated according to Higuchi, samples (40 μL) from each PCR tube are restriction endonuclease digested for 12–16 hours. These products are electrophoresed on a 3% Nusieve, 1% LE agarose ethidium bromide stained gel for 2–3 hrs. at 60 V. A negative photograph is taken of the gel using Polaroid 665 positive/negative instant film.

The negative photograph is subjected to densitometry using, for example, Zeineh Soft Laser Scanning Densitometer Model SLR 2D/1D using Zeineh 1D Autostepover Videophoresis Program Software (Biomed Instruments, Fullerton, Calif.). Alternatively, the stained gel is evaluated densitometrically directly using a digital camera, or evaluated on an automated sequencing gel (such as that offered by Applied Biosystems, Inc.). Areas under each curve are calculated and used for quantification. Corrections are made for relative band sizes and heterodimer formation. Results are expressed as target gene to housekeeping gene relative ratios.

Multiplex competitive PCR improves and simplifies quantitation of gene expression. Gene expression can be quantitated in very small samples of tissue or cells without resorting to radiolabeling. As a result, multiplex reverse transcription PCR is less expensive and safer to use than radiolabeling. The results are reproducible for examples using the same master mixture and dilutions of internal mutated standard competitive templates.

It is to be understood that according to the method of the present invention, all oligonucleotides homologous to each strand of the cDNA of known or potential housekeeping genes (including but not restricted to the human, mouse and rat GAPDH, β-actin, 28S RNA, 18S RNA, and all ribonuclear protein genes) and containing restriction endonuclease recognition site sequences or one or two base pair mismatches for restriction endonuclease recognition sequences are useful in the practice of the present invention. The oligonucleotides are used to prepare competitive templates of housekeeping genes for use in quantitative PCR.

It is to be further understood that according to the method of the present invention, all oligonucleotides that contain sequences homologous to sequences in known or potential housekeeping genes (including but not restricted to GAPDH, β-actin, 28S RNA, 18S RNA, and all ribonuclear protein genes) are useful in generating artificially shortened competitive templates. The oligonucleotides are used to prepare competitive templates of housekeeping genes for use in the present invention.

It is contemplated that uses of this inventive technique include: a) evaluating gene expression from tissues obtained by endoscopic biopsy (brush or forceps), needle aspiration, and bone marrow biopsy; b) quantification of reporter gene expression in transient transfection assays; and c) quantification of transfected genes following gene therapy.

While a method described in Morales, M. J., and Gottlieb, D. I., (A polymerase chain reaction-based method for detection and quantification of reporter gene expression in transient transfection assays, Analytical Biochemistry, 210, 188–194 (1993)), allows measurement of transcription from the reporter gene, it does not control for variation resulting from differences in amount of RNA included in the assay. The method of the present invention is further useful to evaluate simultaneously both the exogenous reporter gene and an endogenous housekeeping gene, such as GAPDH RNA from the transfected cell.

Although numerous different mutations in the cystic fibrosis transmembrane conductance regulator gene (CFTR) have been reported to be associated with disease, the most common disease-associated mutation is a 3 base deletion at position 508. It is possible to prepare oligonucleotide primers that result in amplification of only the abnormal 508 deleted gene or only the normal CFTR gene using recently described methods (Cha, R. S., Zarbl, H., Keohavong, P., Thilly, W. G., match amplification mutation assay (MAMA): application to the c-Ha ras gene, PCR methods and applications, 2:14–20 (1992). It is further contemplated that it is possible to measure the relative amount of exogenous CFTR gene per cell using the method of the present invention. Without comparing the amount of abnormal CFTR to some internal standard, it would not be possible to quantify the efficiency of transfection. The samples are too small to measure RNA by Northern analysis.

The method of the present invention is useful to develop PCR systems for selective amplification of exogenous normal dystrophin gene in the presence of mutated endogenous gene. In the case of dystrophin, the disease results from relatively large deletions. Several different ones have been described. Using the method of the present invention, different PCR systems may be developed for selective amplification of the transfected normal gene and constitutive abnormal gene for each of these cases. This may be done by changing primers that span to the deleted region.

It should be further understood that according to the method of the present invention, more than one gene can be evaluated at the same time.

METHODS

Purified deoxyribonucleotides obtained from Pharmacia (Piscataway, N.J.) were diluted to a stock solution of 10 mM. Recombinant Thermus aquaticus DNA polymerase (Taq polymerase), Avian myeloblastosis virus (AMV) reverse transcriptase, and ribonuclease inhibitor (RNasin) were obtained from Promega (Madison, Wis.). EcoRI enzyme was obtained from USB (Cleveland, Ohio). Primers were prepared on an Applied Biosystems model 391 PCR-Mate EPTM synthesizer. PCR was performed in a Perkins, Elmer, Cetus DNA Thermal Cycler 480. The other buffers and solutions used were from various sources and were molecular biology grade.

Studies were performed on a human papillomavirus-immortalized human bronchial epithelial cell line (BEP2D) (Willey et al, Cancer Res. 5 1:5370–5377, 1990).

The isolation of RNA was as follows: RNA was isolated based on the method described by Chomczynski and Sacchi (Analytical Biochemistry 1 6 2:156–159, 1987) Culture medium was removed from flasks containing the BEP2D cell line. Immediately GIT (4.0M guanidinium thiocyanate, 0.1M Tris Cl Ph=7.5, 1% betamercaptoethanol) buffer was placed on the cells (approximately 500 µL per 5–10 million BEP2D cells). Each 500 µL of GIT buffer containing the lysed cells was then transferred to a 1.5 mL microfuge tube. To each microfuge tube was added sequentially 50 µL of 2M Na acetate pH=4, 500 mL of water saturated phenol and 100 mL of chloroform-isoamyl alcohol mixture (49:1). The tubes then were shaken thoroughly, placed on ice for 15 min, and microcentrifuged for 20 min at 14,000 RPM and 4° C. The aqueous phase of each tube was transferred to a fresh tube and the above extraction was repeated. Again, the aqueous phase of each tube was transferred to a fresh tube with isopropanol (500 µL), and placed at –70° C. for 15 min. The tubes were then microcentrifuged for 20 min at 14,000 RPM and 4° C. The RNA was washed twice with 70% ethanol and vacuum dried. RNA was taken up in 0.1% diethyl pyrocarbonate (DEPC) treated H$_2$O and quantified by spectrophotometry (Gilford Instrument Spectrophotometer 260).

The reverse transcription was conducted as follows: the extracted RNA was placed in a sterile microfuge tube. For each 1 µg of RNA, 0.2 mg oligo dT was added. This was heated at 65° C. for 5 min and placed on ice for one min. To this was added 2 µL 1- mM dNTP's, 2 µL reverse transcriptase (RT) buffer (50.0 mM Tris, 40.0 mM KCl, and 80 mM MgCl$_2$), 0.5 µL RNasin, and 1 µL AMV reverse transcriptase (9.500 units/ml). This was incubated at 42° C. for one hour and heated to 80° C. for 10 min to halt the reaction. Resultant cDNA was stored at –20° C.

The preparation of primers and mutated internal standard competitive templates was as follows: ideal sequences were identified using the Oligo-TM Primer Analysis Software (National Biosciences, Hamel, Mn.). The primers were made using an Applied Biosystems Model 391 PCR-Mate DNA Synthesizer. The primer sequences are described below. Glutathione Peroxidase (GSH-Px) (Chada et al., Genomics 6:268–271, 1990)

The "outer" primers used to amplify both the native and mutated templates result in a product length of 354 base pairs. The "outer" primers are Sequence I.D. No. 1) (Chada et al., Genomics 6:268–271, 1990.)

Pos. 241 5'-GGGCCTGGTGGTGCTTCGGCT-3' (coding sense) correspond to bases 241–261 of the cloned sequence, and Sequence I.D. No. 2) (Apostolakos et al., Anal Biochem. 213:277–284, 1993.)

Pos. 574 5'-CAATGGTCTGGAAGCGGCGGC-3' (anti-coding sense) which anneals to bases 574–594.

The "inner" primers used to synthesize the mutated internal standard remove an EcoRI restriction endonuclease recognition site (GAATTC) by changing a native cDNA base pair (bold bases). The "inner" primers are Sequence I.D. No. 3) (Chada et al., Genomics 6:268–271, 1990.)

Pos. 309 5'-ATTCT GATTTC CCTCAAGTACGTCCGGCCT-3' (coding sense) Sequence I.D. No. 4) (Chada et al., Genomics 6:268–271, 1990.)

Pos. 309 3'-TAAGA CTAAAG GGAGTTCATGCAGGCCGGA-5' (anti-coding sense)

Both primers correspond to bases 309–338 of the cloned sequence. The mutation results from the substitution of a T for the native A at position 316 of the sense strand. Restriction endonuclease digestion of the native GSH-Px yields products of 280 and 74 base pairs. Glyceraldehyde-3-Phosphate Dehydrogenase (GAPDH) (Tso et al., Nucleic Acids Res. 13:2485–2502, 1985)

The "outer" primers used to amplify both the native and mutated templates result in a product length of 788 or 790 base pairs. The "outer" primers are: Sequence I.D. No. 5) (Tso et al., Nucleic Acids Res. 13:2485–2502, 1985.)

Pos. 46 5'-GGTCGGAGTCAACGGATTTGGTCG-3' (coding sense) corresponding to bases 9–32 of the cloned sequence, and Sequence I.D. No. 6) (Tso et al., Nucleic Acids Res. 13:2485–2502, 1985.)

Pos. 812 5'-CCTCCGACGCCTGCTTCACCAC-3' (anti-coding sense) which anneals bases 777–798.

The "inner" primers used to synthesize the mutated template create an EcoRI restriction endonuclease recognition site (GAATTC) by changing one native cDNA base pair (bold bases). The "inner" primers are: Sequence I.D. No. 7) (Tso et al., Nucleic Acids Res. 13:2485–2502, 1985.)

Pos. 234 5'-TGATCAATG GAATTC CCATCACCA-3' (coding sense) Sequence I.D. No. 8) (Tso et al., Nucleic Acids Res. 13:2485–2502, 1985.)

Pos. 234 3'-ACTAGTTAC CTTAAG GGTAGTGGT-5' (anticoding sense)

Both primers correspond to bases 199–222 of the cloned sequence. The mutation results from the substitution of a T for the native A at position 211 of the sense strand. Restriction endonuclease digestion of the mutated GAPDH yields products of 588 and 200 base pairs.

Several experiments were performed using a different mutated GAPDH template. This template had a novel Barnill restriction site introduced.

The "outer" primers used to amplify both the native and mutated templates result in a product length of 634 base pairs. The "outer" primers are: Sequence I.D. No. 9) (Tso et al., Nucleic Acids Res. 13:2485–2502, 1985.)

Pos. 200 5'-CATGGCACCGTCAAGGCTGAGAAC-3' (coding sense) corresponding to bases 165–188 of the cloned sequences, and Sequence I.D. No. 10) (Tso et al., Nucleic Acids Res. 13:2485–2502, 1985.)

Pos. 813 5'-CCTCCGACGCCTGCTTCACCAC-3' (anti-coding sense) which anneals to bases 777–798.

The "inner" primers used to synthesize the mutated template create a Barnill restriction endonuclease recognition site (GGATCC) by changing one native cDNA base pair (bold bases). The "inner" primers are: Sequence I.D. No. 11) (Tso et al., Nucleic Acids Res. 13:2485–2502, 1985.)

Pos. 368 5'-CAGGGG GGATCC AAAAGGGTCATCAT-3' (coding sense) Sequence I.D. No. 12) (Tso et al., *Nucleic Acids Res.* 13:2485–2502, 1985.)

Pos. 368 3'-GTCCCC CCTAGG TTTTCCCAGTAGTA-5' (anticoding sense)

Both primers correspond to bases 333–358 of the cloned sequence. The mutation results from the substitution of a T for the native G at position 342 of the sense strand. Restriction endonuclease digestion of this mutated GAPDH yields products of 460 base pairs and 174 base pairs.

The mutated internal standard competitive templates were prepared by site directed mutagenesis as described by Higuchi et al., *Nucleic Acids Res.* 16:7351–7367, 1988. These single base mutations resulted in either the gain (GAPDH) or loss (GSH-Px) of an EcoRI restriction endonuclease recognition site. (Experiments were also conducted using a muted GAPDH with a BamHI site introduced). For each mutated product, two initial polymerase chain reactions using an "outer" primer and an "inner" single base mismatched primer produce two overlapping DNA fragments. (Primers 1 and 4, 2 and 3 for GSH-Px; Primers 5 and 8, 6 and 7 for GAPDH). These overlapping DNA fragments were electrophoresed on a 3% Nusieve, 1% LE agarose ethidium bromide stained gel. Bands were excised and purified using Millipore Ultrafree-MC 0.45 µM filter (Nihon Millipore Kogyo K.K., Yonezawa, Japan). The purified DNA was ethanol precipitated, washed, vacuum dried and taken up in 100 µL sterile dH2O. 1 µL of each of the two overlapping DNA fragments were PCR amplified using the outer primers only. The first PCR cycle was performed without primers to allow for heterodimer formation. The entire mutated product was thus formed and amplified. The mutated PCR product was gel purified as described above and reamplified to form bulk product. The bulk product was gel purified and measured spectrophotometrically. The mutated products were diluted to the attomolar range for use as competitive templates. Herring sperm DNA (Lofstrand, Bethesda, Md.) 1 µg/ml was used as a carrier. Restriction endonuclease digestion was performed on samples of each mutated template to assure lack of contamination.

The PCR conditions were as follows: The PCR conditions were standardized for each experiment by using a master mixture containing 1× PCR buffer (50 mM KCl, 10 mM Tris-HCl, pH 9.0, 1.5 mM MgCl$_2$), 25 pmoles of primers coding for GSH-Px and GAPDH, 0.2 mM dNTP's (A,T,C, G), and constant amounts of both internal standards per 100 µL reaction mixture. Taq DNA polymerase (2.5 units) was added to each 100 µL reaction prior to amplification. cDNA obtained from the BEP2D cell line was serially diluted and added to the sample PCR tubes. In all experiments, control tubes containing no template, native cDNA only, or mutated standards only were amplified to check for contamination or complete enzyme digestion.

PCR amplification was carried out for 35 cycles at 94° C. for one min, 60° C. for one min, and 72° C. for one min. After amplification, PCR products were heated for 10 min in order to maximize heterodimer formation.

The quantification of products was as follows: Samples (40 µL) for each PCR tube were EcoRI restriction endonuclease digested for 12–16 hours (Experiments conducted using mutated GAPDH with the novel Barnill restriction site were also Barnill restriction endonuclease digested for 4–5 hours). These products were isolated by electrophoresing on a 3% Nusieve, 1% LE agarose ethidium bromide stained gel for 2–3 hours at 60 V. A negative photograph was taken of the gel using Polaroid 665 positive/negative instant film.

The negative photograph was subjected to densitometry (Zeineh Soft Laser Scanning Densitometer Model SLR 2D/1D using Zeineh 1D Autostepover Videophoresis Program Software, Biomed Instruments, Fullerton, Calif.). Areas under each curve were calculated and used for quantification. Corrections were made for relative band sizes and heterodimer formation. Data were expressed GSH-Px to GAPDH relative ratios.

In a second set of experiments, multiplex competitive reverse transcriptase polymerase chain reaction (MC RT-PCR) with competitive templates were prepared by the Cell method to evaluate the cytochrome p450 (CYP) IAI gene in β-napthoflavone-exposed BEP2D cells. The induction of CYPIAI gene expression was evaluated using both MC RT-PCR with Cell competitive templates, and Northern analysis. Competitive templates were prepared for both the CYPIAI and GAPDH genes. The primers used to prepare the competitive template for GAPDH were: Sequence I.D. No. 13) (Tokunaga et al., *Cancer Res.* 47:5616–5619, 1990.)

Pos. 75 5'-GGT CGG AGT CAA CGG ATT TGG TCG-3' Pos. 94 and: Sequence I.D. No. 14) (Tokunaga et al., *Cancer Res.* 47:5616–5619, 1990.)

Pos.822\ /Pos.636
Pos.842 5'-CCT CCG ACG CCT GCT TCA C<u>CC</u> CAT CAC GCC ACA GTT TCC C-3'Pos.616

The lower outer primer used in conjunction with Sequence I.D. No. 13 to amplify both the competitive and native templates was Sequence I.D. No. 15) (Tokunaga et al., *Cancer Res.* 47:5616–5619, 1990.)

Pos. 842 5'-CCT CCG ACG CCT GCT TCA CC-3' Pos. 822

The primers used to prepare the competitive template for CYPIAI were: Sequence I.D. No. 16) (Jaiswal et al., *Science* 228:80–83, 1989.)

Pos. 1241 5'-CAT CCC CCA CAG CAC AAC AAG-3' Pos. 1262 and: Sequence I.D. No. 17) (Jaiswal et al., *Science* 228:80–83, 1989.)

Pos.1555\ /Pos.1428
Pos.1575 5'-ACA GCA GGC ATG CTT CAT G<u>GG</u> TCT CAC CGA TAC ACT TCC G-3'Pos.1448

The lower outer primer used in conjunction with Sequence I.D. No. 18 to amplify both the competitive and native templates was Sequence I.D. No. 18) (Jaiswal et al., *Science* 228:80–83, 1989.)

Pos. 1575 5'-ACA GCA GGC ATG CTT CAT GG-3' Pos. 1555

The PCR amplication conditions were the same as described for experiments using the competitive templates prepared for GAPDH and GSHPx by the Higuchi method except the annealing temperature was 55 degress centrigrade and the amplification was carried out for 38 cycles.

Because the native and competitive templates separate without prior restriction endonuclease digestion, samples were taken directly from the PCR reaction tube and applied to ethidium bromide stained 3% Nusieve, 1% LE agarose gels. It was then possible to quantify the products by taking a negative photograph of the gel using Polaroid 665 positive/negative instant film, subjecting the negative photograph to densitometry.

RNA from BEP2D cells incubated for varying time with β-napthoflavone (10 µM) was either electrophoresed on a 1% LE formaldehyde denaturing gel for Northern analysis or MC RT-PCR amplified, as decribed above. For Northern analysis, following transfer of the RNA to GeneScreen, the filters were hybridized with $^{32}$P-labeled CYPIAI cDNA.

RESULTS

Figure 2:
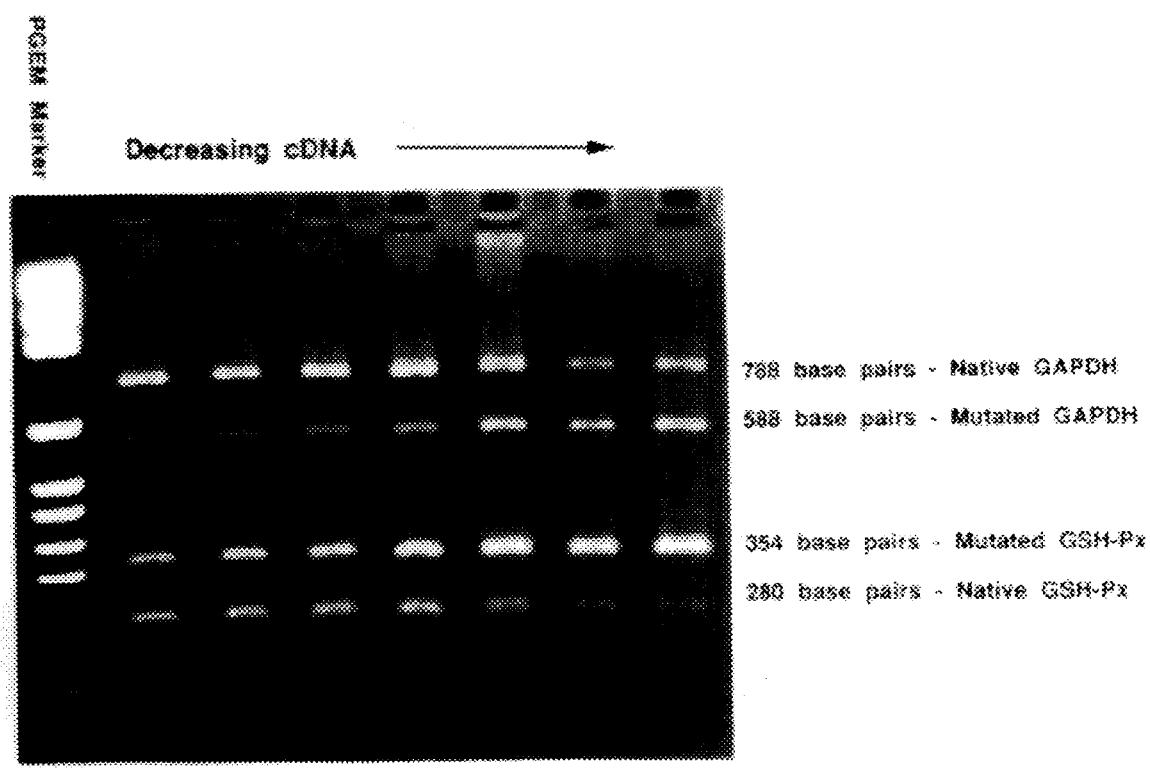
FIG. 2 is a photograph showing serial dilutions of BEP2D human papillomavirus-immortalized human bronchial epithelial cell line cDNA (representing 0.25 μg to 0.05 μg total RNA) that were co-amplified with constant amounts of each single base mutated internal standard (10 attamoles each), subjected to EcoRI restriction endonuclease digestion and electrophoresed on an agarose gel. A negative photograph of this gel was then subjected to densitometry in order to quantify bands.

The procedure used for PCR quantitation is shown schematically in FIG. 1. Serial dilutions of BEP2D cDNA (representing 0.25 μg to 0.05 μg total RNA) were co-amplified with constant amounts of each single base mutated internal standard (10 attamoles each), then analyzed as described above. A negative photograph of the gel was analyzed by densitometry in order to quantify each band, as seen in FIG. 2.

Using the area under each curve, relative ratios between native/mutated products were obtained. Corrections were made for relative band sizes (i.e. mutated GAPDH was multiplied by 788/588 when compared to native GAPDH and native GSH-Px was multiplied by 354/280 when compared to mutated GSH-Px). Heterodimer formation was maximized following PCR by heating the products to 100° C. for 10 min followed by slow cooling. Following maximization of heterodimers, the quantity of each product was determined by analysis of the densitometric data using the quadratic formula as the formation of heteroduplexes follows a binomial distribution under these conditions (Gilliland et al, Proc. Natl. Acad. Sci. 87:2725–2729 (1990), Becker-Andre et al., *Nucleic Acids Res.* 17:9437–9446 1989). Final values were expressed as an odds ratio of GSH-Px native/mutated to GAPDH native/mutated. While the graph, shown in FIG. 3, of the amount of native product (in arbitrary densitometric units) vs. total starting RNA did not remain linear throughout for either GSH-Px or GAPDH, the graph of the ratios of GSH-Px native/mutated vs. total starting RNA and GAPDH native/mutated vs. total starting RNA was linear for both genes. By averaging the ratio obtained from each sample tube (2.18:1, 1.14:1, 2.00:1, 1.76:1, 2.46:1, 2.71:1, and 1.92:1), a mean value of the ratio GSH-Px native/mutated to GAPDH native/mutated of 2.17:1 with a S.D. of 0.33 was obtained. No value varied more than 25% from the mean.

To assess the variability of this technique, a repeat of the above experiment was performed using different dilutions of mutated standards and master mixture. By averaging the ratio obtained from each sample tube (1:9.09, 1:8.13, 1:9.43, 1:8.13, 1:6.62, 1:8.77, 1:7.69, 1:10.00, 1:7.58, and 1:7.04), a mean value of the ratio of GSH-Px native/mutated to GAPDH native/mutated of 1:8.25 with a S.D. of 1.07 was obtained. No value varied more than 22% from the mean. This confirms the precision of this technique and also illustrates the variability introduced by new master mixtures containing new dilutions of mutated standards.

To assess the variability between samples using the same master mixture and dilutions of mutated standards, BEP2D RNA was independently extracted from three separate flasks and reverse transcribed to cDNA. Only coarse (5 fold) dilutions of cDNA were performed. Four PCR tubes were run for each study. The obtained ratios of GSH-Px native/mutated to GAPDH native/mutated were 15.01:, 17.69:1, and 21.76:1 (mean=18.15, S.D.=3.40). All 3 values were within 20% of the mean. This confirms the precision of this technique when comparing samples that have been independently reverse transcribed but amplified with the same master mixture and internal standard dilutions.

Northern analysis of BEP2D RNA reveals a ratio of GSHPx/GAPDH mRNA of approximately 1:8.

EXAMPLE

Serial dilutions of BEP2D cDNA were co-amplified with constant amounts of each single base mutated internal standard competitive templates (10 attomoles each), and then evaluated. Negative photographs of the gels (shown in FIG. 2) were analyzed by densitometry in order to quantify each band.

Starting with the area under each curve obtained by the densitometric evaluation of the bands, the ratios of native/mutated products were calculated as follows. Data were evaluated from one gene at a time. Corrections were made for relative band sizes. (Mutated GAPDH was multiplied by 788/588 when compared to native GAPDH and native GSH-Px was multiplied by 354/280 when compared to mutated GSH-Px). During PCR, under conditions in which primer is limiting, heterologous single strands of DNA with sequence homology may anneal to form heterodimers (Gilliland, G., Perrin, S., Blanchard, K. and Bunn, H. F. (1990) *Proc. Natl. Acad. Sci.* 87:2725–2729). When the heterologous strands differ by only one base pair, as in this invention, the heterologous strands re-anneal randomly (Gilliland et al., supra; Thompson, J. D., Brodsky, I., and Yunis, J. J. (1992) *Blood* 79:1629–1635), as shown in the Punnett square below:

|   | N  | M  |
|---|----|----|
| N | NN | NM |
| M | NM | MM |

Where N=the proportion of single-stranded native product prior to re-annealing, M=the proportion of single-stranded mutated product prior to re-annealing, NN (or $N^2$)=the proportion of double-stranded native product after re-annealing, 2NM=the proportion of heterodimer formed after re-annealing, and MM (or $M^2$)=the proportion of double-stranded mutated product after re-annealing.

Heterodimers were accounted for indirectly because they were not cut by the restriction enzyme and had the same electrophoretic mobility as the undigested homodimer. Therefore, heterodimers were read densitometrically along with the undigested homodimer. In order to quantitate products based on the Punnett square distribution, random heterodimer formation was ensured following PCR. This was done (according to the methods described in Gilliland et al., supra, and Thompson et al., supra), by heating the products to 100° C. for 10 min. followed by slow cooling.

For GAPDH, neither the native product (NN) nor the heterodimer (NM) were cleaved by EcoRI. Therefore, the larger band represented both native GAPDH homodimer (NN) and the NM heterodimer. This band was presented arithmetically by $N^2+2NM$, according to the Punnett square, while the proportion in the band resulting from EcoRI cleavage was represented by the value $M^2$. Therefore, when the amount of native (N) and mutated (M) template are equal (1:1) prior to PCR, after heterodimer formation is randomized, the apparent ratio will be 3:1 [$N^2+2NM$]: $M^2$]. To illustrate this further, the raw densitometric data from the first sample lane (shown in FIG. 2) are shown in Table 1 and are mathematically processed to final ratios below:

The value of $M^2$ is known (2,214), as is the value of $N^2+2NM$ (10,095). From this information, M is calculated (47.05) and solving for N results in quadratic equation ($aX^2+bX+c=0$):

$$N^2+2N(47.05)-10,095=0$$

The quadratic formula ($N=-b+/-\sqrt{b^2-4ac}/2a$) is used to solve for N. In this case, a=1, b=94.1, c=10,095, and thus N=63.89. The information sought is the ratio N/M which is 63.89/47.10 or 1.36/1. (Although proportions of single-stranded DNA present after PCR are solved for, they are identical to those of the corresponding double-stranded DNA present prior to the PCR.)

Since densitometric values are relative, it is possible to avoid the inconvenience of using the quadratic formula by assigning the bands proportionate densitometric values that when added=1 or $(N^2+2NM)+M^2=1$. Solving for this equation:

$(N^2+2NM)+M^2=(N-M)^2=1$ and therefore $N+M=1$

The relative fractions of 1 assigned to each of the bands is determined by their respective densitometric values (Table 1). Since the total densitometric value of both bands is 12,309 (10,095+2,21 4), the relative proportion of the larger band $(N^2+2NM)$ is 0.82 (10,095/12,309) and the relative proportion of the smaller band $(M^2)$ is 0.18 (2,214/12,309). Thus, the proportion of mutated GAPDH homodimer $(M^2)$ is 0.18, and the proportion of single-stranded mutated GAPDH (M) is 0.424. Since N+M =1, the proportion of single-stranded native GAPDH (N) is 1−0.424 or 0.576, and the ratio of native to mutated product is 0.576/0.424 or as calculated above 1.36/1.

TABLE 1

Densitometric Data from First Sample Lane of FIG. 2

| | Length (base pairs) | Zeineh densitometric values | Size correction | Relative densitometric values |
|---|---|---|---|---|
| (A) GAPDH | | | | |
| Native GAPDH and heterodimer $(N^2 + 2NM)$ | 788 | 10,095 | | 0.820 |
| Mutated GAPDH $(M^2)$ | 588 | 1,652 | X788/588 = 2214 | 0.180 |
| (B) GSH-Px | | | | |
| Mutated GSH-Px and heterodimer $(M^2 + 2MN)$ | 354 | 6,709 | | 0.442 |
| Native GSH-Px $(N^2)$ | 280 | 6,692 | X354/280 = 8461 | 0.558 |

Next, the same calculations are carried out using the densitometric values for native and mutated GSH-Px from the same lane as the GAPDH values above (Table 1):

$N^2=0.558$, $N=0.747$, and $M=1-0.747=0.253$

Native/mutated ratios are obtained:

GSH-Px native/mutated=0.747/0.253=2.95/1

GAPDH native/mutated=0.576/0.424=1.36/1

And, final odds ratios are reported:

GSH-Px native/mutated: GAPDH native/mutated=2.95/1.36=2.17/1

As shown above, final values were expressed as an odds ratio of GSH-Px native/mutated to GAPDH native/mutated. While the relationship between the amount of native product (in arbitrary densitometric units) and total starting RNA did not remain linear throughout for either GSH-Px or GAPDH (as shown in FIG. 3), the relationship of the ratios GSH-Px native/mutated and GAPDH native/mutated to total starting RNA was linear for both genes (as shown in FIG. 4). By averaging the ratio of GSH-Px native/mutated to GAPDH native/mutated obtained from sample tube (2.17:1, 2.14:1, 2.00:1, 1.76:1, 2.46:1, 2.71:1, and 1.92:1), a mean value of 2.17:1 with a S.D. of 0.33 was obtained. No value varied more than 25% from the mean.

To assess the variability of this technique, the experiment was repeated using different dilutions of mutated standards and master mixture. By averaging the ratio of GSH-Px native/mutated to GAPDH native/mutated obtained from each sample tube (1:9.09, 1:8.13, 1:9.43, 1:8.13, 1:6.62, 1:8.77, 1:7.69, 1:10.00, 1:7.58, and 1:7.04), a mean value of 1:8.25 with a S.D. of 1.07 was obtained. No value varied more than 22% from the mean.

To assess the variability between samples using the same master mixture and dilutions of mutated standards (using mutated GAPDH with novel Barnill restriction site), BEP2D RNA was independently extracted from three separate flasks and reverse transcribed to cDNA. Five fold dilutions of cDNA were performed. Four PCR tubes were run for each study. The obtained ratios of GSH-Px native-mutated to GAPDH native/mutated were 15.01:1, 17.69:1, and 21.76:1. (mean=18.15, S.D.=3.40). All 3 values were within 20% of the mean.

Figure 5A:
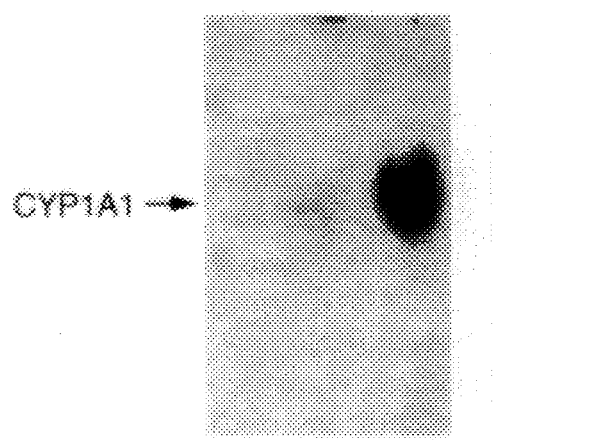
FIG. 5 is a photograph showing a) Northern analysis of RNA obtained from BEP2D cells that were treated with 0.1% DMSO as a control, or β-napthoflavone in an effort to induce cytochrome p450 IA1 (CYPIA1); and b) DNA PCR-amplified from serial dilutions of cDNA from the same cells as in a. The cDNA was co-amplified in the presence of competitive template internal standards for GAPDH and CYPIAI and oligonucleotide primers for these genes.
Figure 5B:
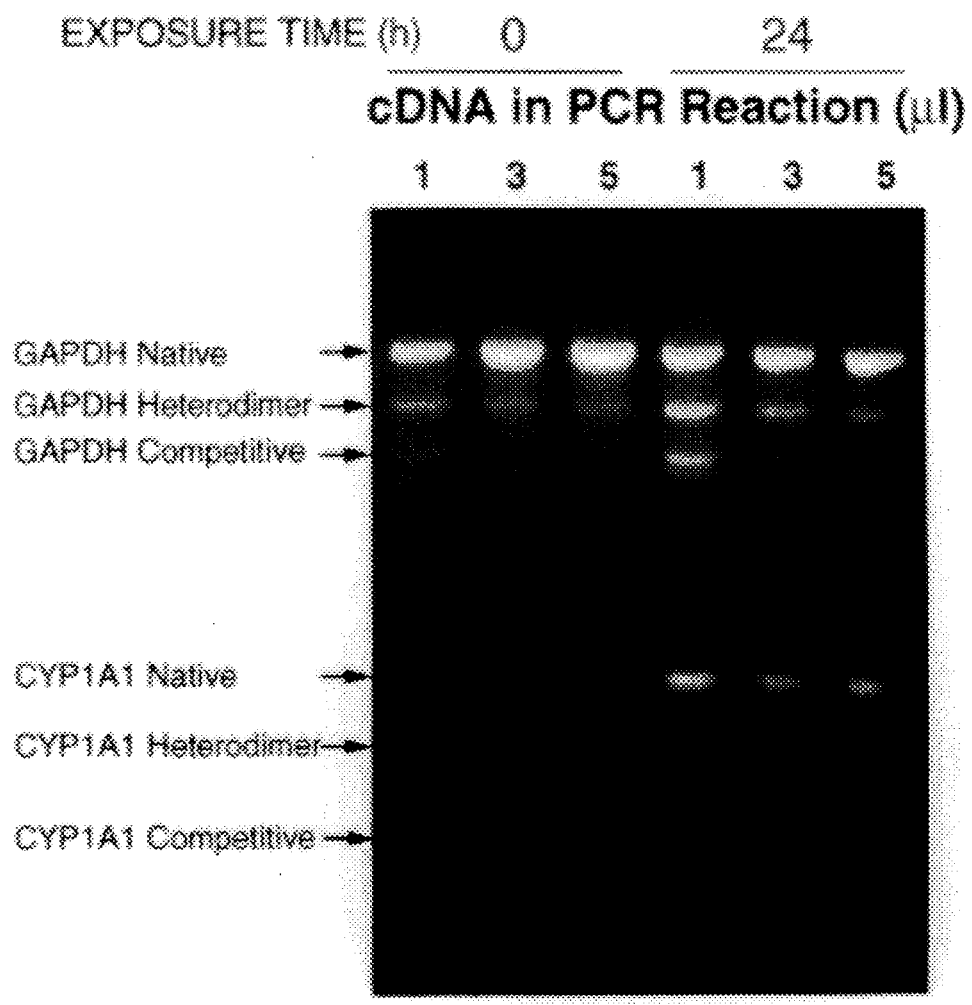

The CYPIAI gene expression was observed in both Northern and MC RT-PCR analysis to approximately the same degree, as seen in FIG. 5. By comparing the bands of the GAPDH housekeeping gene representing native and competitive template cDNA, it is clear that approximately the same amount of cDNA was loaded in the lane with 1 ul of sample from control cells and the lane with 3 ul of sample from β-napthoflavone exposed cells. Having determined which lanes were loaded the same, it is then clear that the band representing the native CYPIAI gene is much more strongly represented in the lane containing cDNA from β-napthoflavone exposed cells compared to control cells.

---

What is claimed:

1. A kit for quantitatively measuring gene expression of a target gene of interest comprising at least one pair of primers for amplification of the target gene; at least one pair of primers for amplification of a housekeeping gene; at least one competitive template of the target gene; and at least one competitive template of the housekeeping gene wherein the competitive templates of the target gene and the housekeeping gene differ from the target gene and the housekeeping gene, respectively, by at least a point mutation.

2. The kit of claim 1, wherein the primers of the housekeeping gene comprise the sequences of Sequence I.D. No. 5 and Sequence I.D. No. 6.

3. The kit of claim 1, wherein the competitive template of the housekeeping gene comprises the sequences of Sequence I.D. No.5, Sequence I.D. No. 6, Sequence I.D. No. 7 and Sequence I.D. No. 8.

4. The kit of claim 1, wherein the oligonucleotide primers of the housekeeping gene comprise the sequences of Sequence I.D. No. 13 and Sequence I.D. No. 15.

5. The kit of claim 1, wherein the primers of the housekeeping gene comprise the sequences of Sequence I.D. No. 13 and Sequence I.D. No. 15.

6. The kit of claim 1, wherein the primers of the target gene comprise the sequences of Sequence I.D. No. 16 and Sequence I.D. No. 18.

* * * * *

UNITED STATES PATENT AND TRADEMARK OFFICE
CERTIFICATE OF CORRECTION

PATENT NO : 5,639,606
DATED : June 17, 1997
INVENTOR(S): James C. Willey

It is certified that error appears in the above-identified patent and that said Letters Patent are hereby corrected as shown below:

IN THE ABSTRACT

The abstract is supposed to read:

A method for quantitative measurement of gene expression through multiplex competitive reverse transcriptase polymerase chain reaction amplification has been established which comprises isolating cellular mRNA of a target gene and a housekeeping gene which are then reverse transcribed and specifically amplified in the presence of competitive templates such that a ratio of target to housekeeping gene is obtained and used to assess the amount of gene expression. This method is useful for analysis of the small specimens (cells and tissues) available from human subjects and allows improved understanding of mechanisms of disease.

In Col. 5, line 1, delete "-sphosphate dehydrogenase" and insert --3-phosphate dehydrogenase)--.

UNITED STATES PATENT AND TRADEMARK OFFICE
CERTIFICATE OF CORRECTION

PATENT NO : 5,639,606
DATED : June 17, 1997
INVENTOR(S): James C. Willey

It is certified that error appears in the above-identified patent and that said Letters Patent are hereby corrected as shown below:

In Col. 5, line 2, delete the parenthesis following the term "GSH-Px".

In Col. 6, line 12, delete "Cell" and insert --Celi--.

In Col. 8, line 67, delete "changing" and insert --choosing--.

In Col. 10, line 11, delete "GATTTC" and insert --GATTTC--.

In Col. 10, line 14, delete "CTAAAG" and insert --CTAAAG--.

In Col. 10, line 39, delete "GAATTC" and insert --GAATTC--.

In Col. 10, line 42, delete "CTTAAG" and insert --CTTAAG--.

In Col. 10, lines 50-51, delete "Bar-nill" and insert --BamHI--.

In Col. 10, line 64, delete "Barnill" and insert --BamHI--.

In Col. 11, line 1, delete "GGATCC" and insert --GGATCC--.

UNITED STATES PATENT AND TRADEMARK OFFICE
CERTIFICATE OF CORRECTION

PATENT NO : 5,639,606
DATED : June 17, 1997
INVENTOR(S): James C. Willey

It is certified that error appears in the above-identified patent and that said Letters Patent are hereby corrected as shown below:

In Col. 11, line 4, delete "CCTAGG" and insert --CCTAGG--.

In Col. 11, line 62, delete "Barnill" and insert --BamHI--.

In Col. 11, line 63, delete "Barnill" and insert --BamHI--.

In Col. 12, line 12, delete "Cell" and insert --Celi--.

In Col. 12, line 15, delete "Cell" and insert --Celi--.

In Col. 12, line 51, at the beginning of the paragraph, insert --The shortened competitive templates separate from the native templates during electrophoresis.--.

In Col. 13, line 56, delete "15.01:," and insert --15.01:1,--.

In Col. 14, line 52, delete the comma following the term "$M^2$" and insert a period --.-- instead.

In Col. 15, line 15, delete the space mistakenly included between the numbers "1" and "4".

UNITED STATES PATENT AND TRADEMARK OFFICE
CERTIFICATE OF CORRECTION

PATENT NO : 5,639,606
DATED : June 17, 1997
INVENTOR(S): James C. Willey

It is certified that error appears in the above-identified patent and that said Letters Patent are hereby corrected as shown below:

In Col. 16, line 31, delete "Barnill" and insert --BamHI--.

IN THE CLAIMS

Delete claim 4. Renumber claims 1,2,3,5, and 6, as 1,2,3,4, and 5.

Insert claim 6, as follows:

6. The kit of claim 1, wherein the competitive templates comprise the sequences of Sequence I.D. No. 16 and Sequence I.D. No. 17.

Signed and Sealed this

Nineteenth Day of May, 1998

Attest:

BRUCE LEHMAN

Attesting Officer

Commissioner of Patents and Trademarks